(12) United States Patent
Garg

(10) Patent No.: US 11,311,370 B2
(45) Date of Patent: Apr. 26, 2022

(54) SYSTEM AND METHOD OF MANUFACTURING PROSTHESES

(71) Applicant: Prayasta 3D Inventions Pvt Ltd, Karnataka (IN)

(72) Inventor: Vikas Garg, Karnataka (IN)

(73) Assignee: PRAYASTA 3D INVENTIONS PVT LTD, Karnataka (IN)

( * ) Notice: Subject to any disclaimer, the term of this patent is extended or adjusted under 35 U.S.C. 154(b) by 86 days.

(21) Appl. No.: 16/980,969

(22) PCT Filed: Mar. 16, 2019

(86) PCT No.: PCT/IN2019/050212
§ 371 (c)(1),
(2) Date: Sep. 15, 2020

(87) PCT Pub. No.: WO2019/175901
PCT Pub. Date: Sep. 19, 2019

(65) Prior Publication Data
US 2021/0267750 A1 Sep. 2, 2021

(30) Foreign Application Priority Data
Mar. 16, 2018 (IN) .............................. 201841009689

(51) Int. Cl.
*A61F 2/12* (2006.01)
*B33Y 80/00* (2015.01)
(52) U.S. Cl.
CPC ................ *A61F 2/12* (2013.01); *B33Y 80/00* (2014.12); *A61F 2210/0076* (2013.01); *A61F 2240/002* (2013.01)

(58) Field of Classification Search
CPC .............. A61F 2/12; A61F 2210/00076; A61F 2240/002; B33Y 80/00
(Continued)

(56) References Cited

U.S. PATENT DOCUMENTS 6,564,086 B2 5/2003 Marchitto et al.
7,875,074 B2 1/2011 Chen et al.
(Continued)

FOREIGN PATENT DOCUMENTS

WO WO2017080664 5/2017

OTHER PUBLICATIONS

PCT International Search Report, and Written Opinion for corresponding PCT Application No. PCT/IN2019/050212, dated Jun. 20, 2019, 8 pages.

*Primary Examiner* — Suzette J Gherbi
(74) *Attorney, Agent, or Firm* — Dority & Manning, P.A.

(57) ABSTRACT

Embodiments here provide a method of manufacturing including steps of determining a dimension of a three dimensional prosthesis wherein an external contour matches the three dimensional contour of the anatomical structure of the person and a three dimensional internal architecture is incorporated that includes of a plurality of void spaces separated by a plurality of internal walls wherein the three dimensional internal architecture is selected to match the first Young's modulus of elasticity specific to the anatomical structure of the person and the prosthesis is dispensed layer by layer using additive manufacturing technique. Filler material is chosen in filled in at least one of the plurality of void spaces separated by a plurality of internal walls. The desired elastic and mechanical properties close to natural anatomical structure of a person is achieved.

10 Claims, 5 Drawing Sheets

(58) Field of Classification Search
USPC .......................................................... 623/7–8
See application file for complete search history.

(56) References Cited

U.S. PATENT DOCUMENTS

| | | |
|---|---|---|
| 8,231,634 B2 | 7/2012 | Mahfouz et al. |
| 2021/0052367 A1* | 2/2021 | Yang .......................... A61F 2/00 |
| 2021/0145608 A1* | 5/2021 | Herr ........................ A61B 5/004 |
| 2021/0267750 A1* | 9/2021 | Garg ....................... B33Y 80/00 |

* cited by examiner

SYSTEM AND METHOD OF MANUFACTURING PROSTHESES

BACKGROUND

Technical Field

The embodiments herein generally relate to prostheses, and, more particularly, to a bio-mimicking prosthesis.

Description of the Related Art

Prostheses are manufactured to replace any lost or missing anatomical structure of a human body. It is of importance for the compliance and physiological and psychological health of a person that the prosthesis looks and feels as close to natural anatomy as possible. Breast prostheses are used to replace, restore or enhance the breast size and shape which may be required due to underdevelopment of breasts naturally, congenital defects, asymmetricity, accident or surgical removal of breasts due to breast cancer. Breast removal due to breast cancer has been one of the most important reasons for women opting for breast prostheses.

Naturally, the breast prostheses should restore the desired shape, size and contour; whether natural or augmented. Also, another requirement is to make the breast prostheses safe for use inside the body for long term without any risks to the health of the person, free of side effects like inflammation or immune rejection, and should not cause any discomfort to the persons. For external breast prostheses, health risks like safety or inflammation are negligible. However, discomfort to the person while wearing the breast prostheses still remains an important requirement. Esthetics and natural feel are also important considerations for breast prostheses.

Traditionally, there have been silicone breast prostheses in use. A special class of silicone is the material of the choice for it's inert properties in biological environment. Currently available breast prostheses comprise of a thin silicone shell which is filled with either silicone gel or saline. The breast prostheses that are available in the market which have certain issues related to suitability to the persons in terms of shape, size and contour or safety or comfort or all of them.

Currently, breast prostheses are available in standard shapes, sizes and contour which may not resemble the natural shape, size and contour of the normal breast on the other side. Restoration of symmetry between the normal and implanted breast is crucial for the person as it affects their body image and in turn self-esteem. Also, elastic properties of breast prostheses are purely derived from the silicone material used which may or may not match the elastic properties of normal breast tissue. If not matched, it negatively affects the touch and feel of the breasts with prostheses. Also, weight of the breast prostheses is dependent on density of the silicone material used for given size currently and may not be tailored as per person's requirements. In long term, imbalance of two breasts causes discomfort in day to day activities of the persons. Also, shell of the breast prostheses or prostheses may leak due to manufacturing defects or in response to an impact during an accident which releases the silicone gel material in the person's body which causes excessive pain and discomfort to the person. In case of saline filled prostheses, leaked saline gets absorbed in the body without any pain. However, purpose of the prostheses is considered to be failed and the remaining silicone shell needs to be taken out immediately.

Attempts have been made to make the breast prostheses more person specific, personalized, safe and comfortable. In one of such approach, a scaffold is manufactured as per person's shape and size and later on filled with fat obtained from person's himself But the breast scaffolds have its own drawbacks such as shrinking of fat after implantation, and no guarantee of restoration of shape as scaffold dissolved with time. Also, this approach is not safe for breast cancer persons as they may retain stem cells along with the fat cells which may grow into cancerous mass later on. Another existing prosthesis offers 3D printed, personalized dome shaped breast scaffold with stem cells which guarantees of restoration of shape. However, presence of stem cells in fat may cause recurrence of breast cancer. Also, both these approaches use numerous compounds that are biologically active such as growth factors. Long term response for use of such biologically active components is not well understood in the existing art and its efficacy is debatable, especially for persons with a history of breast cancer There aren't significant attempts to address the above said drawbacks and there is a need for personalization in breast prostheses made of biocompatible and biologically inert silicone material. Existing breast prostheses or prostheses offer two different shapes: (a) hemispherical and (b) teardrop or anatomical, but with no personalization. There are attempts to offer different sizes but only the base dimensions and the projection of the prosthesis are considered, not the whole contour. Another existing breast prosthesis offers a rib like supporting structure in breast, which restores the projection of the breast from sagging, eliminating the risks of leakage but do not restore the shape of the original breast.

One group of existing prostheses contain silicone gel, and they have the risk of leakage of silicone inside the body due to rupture of shell. This exposes the person to silicone gel material that can even be fatal in some cases. Another group of prostheses contain silicone gel with high viscosity, which reduces the risk of leakage but they are heavy in weight thus reducing the comfort.

Further in traditional manufacturing methods, long duration of time as well as high costs are involved for a single prosthesis when attempts are made for personalization according to the person. Same is true for external prostheses as well. Conventionally, a thin shell of silicone is created by dipping a mandrel in the silicone mixture and followed by curing of silicone mixture either at room temperature or elevated temperatures. This steps can be repeated multiple times as per the manufacturer's requirements. Shape and size of the prosthesis depends on the shape and size of the mandrel used. Silicone shell is later filled with silicone gel or saline and sealed to form a breast prosthesis. For external prostheses, similar process is followed using a lower grade of silicone which is biocompatible and safe for short term use outside the body. Conventional manufacturing method have limitations as no internal patterns or architectures can be created using the conventional manufacturing method. Also, elastic properties and hence feel of the prosthesis can't be changed in the conventional manufacturing method.

Accordingly, there remains a need for personalized prostheses to overcome aforementioned drawbacks and also there is a need to improve the manufacturing method as many drawbacks are inherent to the traditional manufacturing methods.

DETAILED DESCRIPTION OF PREFERRED EMBODIMENTS

The embodiments herein and the various features and advantageous details thereof are explained more fully with reference to the non-limiting embodiments. In view of the foregoing, an embodiment herein provides a breast prosthesis or prosthesis containing an internal architecture which is made using a biocompatible and safe prosthesis material. This unique internal architecture of the prosthesis can be tailored to achieve the desired elastic properties, hence the touch and feel close to natural breast of the person. At the same time, it eliminates the need for gels or fluids inside the prosthesis, thus eliminating the risk of leakage when implanted into the person's body. Also, the internal architecture of the prosthesis reduces an overall weight of the prosthesis and can be tuned as per the person's requirements irrespective of the material density.

Prosthesis is either internal or external to the body. Breast implants are also referred as breast prostheses or internal breast prostheses where breast shaped structure made up of biocompatible material is surgically inserted into the body and stays there permanently or for long durations like 5-15 years. Breast prostheses are also referred as external breast prostheses where breast shaped structures are pasted or kept on the skin or worn inside an undergarment on daily basis. These can be used or removed as and when required and do not require any surgical intervention.

In an embodiment, a method of manufacturing a prosthesis includes the steps of obtaining a three-dimensional contour and elastic properties of an anatomical structure of a person, wherein the three dimensional contour is generated using a 3D imaging data, obtaining a first Young's modulus of elasticity specific to the anatomical structure of the person, obtaining a first weight of the anatomical structure of the person, determining a dimension of a three dimensional prosthesis wherein an external contour matches the three dimensional contour of the anatomical structure of the person and a three dimensional internal architecture comprises a plurality of empty spaces also referred to as void spaces separated by a plurality of internal walls wherein the three dimensional internal architecture is selected to match the first Young's modulus of elasticity specific to the anatomical structure of the person by (a) selecting a void size; a void shape; and an internal wall thickness for the plurality of void spaces or (b) determining a category of three dimensional internal architecture based on at least one of (i) the first weight of an anatomical structure and (ii) the first Young's modulus of elasticity for the anatomical structure, dispensing a homogenized biocompatible mixture layer by layer to form the three dimensional prosthesis, wherein the homogenized biocompatible mixture is deposited according to the dimension of a three dimensional prosthesis, selecting at least one void space to fill with a filler material from the plurality of void spaces.

In some embodiments, the prosthesis is made up of an prosthesis grade silicone that is biocompatible and safe for long term use in the human body.

In some embodiments, the homogenized mixture is silicone and cross linker in a ratio of 1:1 to 100:1.

In some embodiments, the method of manufacturing a prosthesis includes (a) capturing the 3D contour and 3D imaging data using the anatomy of a body part to be replaced or (b) capturing the 3D contour and 3D imaging data using the anatomy of an existing symmetrical body part.

In some embodiments, the first weight of the anatomical structure of the person is matched to a second weight of the three dimensional prosthesis.

In another embodiment, anatomical structure to be replaced is a breast tissue wherein the isotropic Young's modulus of the breast tissue ranges from 1.5 Kilo Pascal (kPa) to 12.0 kPa.

In some embodiments, dispensing the homogenized mixture further includes steps of (a) a silicone elastomer through a first extruder using a first miniaturized progressive cavity pump; (b) a cross-linker through a second extruder using a second miniaturized progressive cavity pump into a static homogenizer mixer for homogenization; and (c) depositing form a prosthesis by depositing one layer on another layer starting from a broader dimension of the prosthesis.

In some embodiments, internal walls of the prosthesis have an average perpendicular distance in a range of 2 mm to 50 mm.

In some embodiments, the internal wall thickness is in a range of 0.2 mm to 1.0 mm.

In some embodiments, the category of three dimensional internal architecture is determined from (a) high elastic, low weight; (b) high elastic, medium weight; (c) high elastic, high weight; (d) medium elastic, low weight; (e) medium elastic, medium weight; (f) medium elastic, high weight; (g) low elastic, low weight; (h) low elastic, medium weight; and (i) low elastic, high weight.

In some embodiments, a prosthesis is obtained from the method of manufacturing as described elsewhere herein.

BRIEF DESCRIPTION OF THE DRAWINGS

The embodiments herein will be better understood from the following detailed description with reference to the drawings, in which.

DETAILED DESCRIPTION OF DRAWINGS

Figure 1:
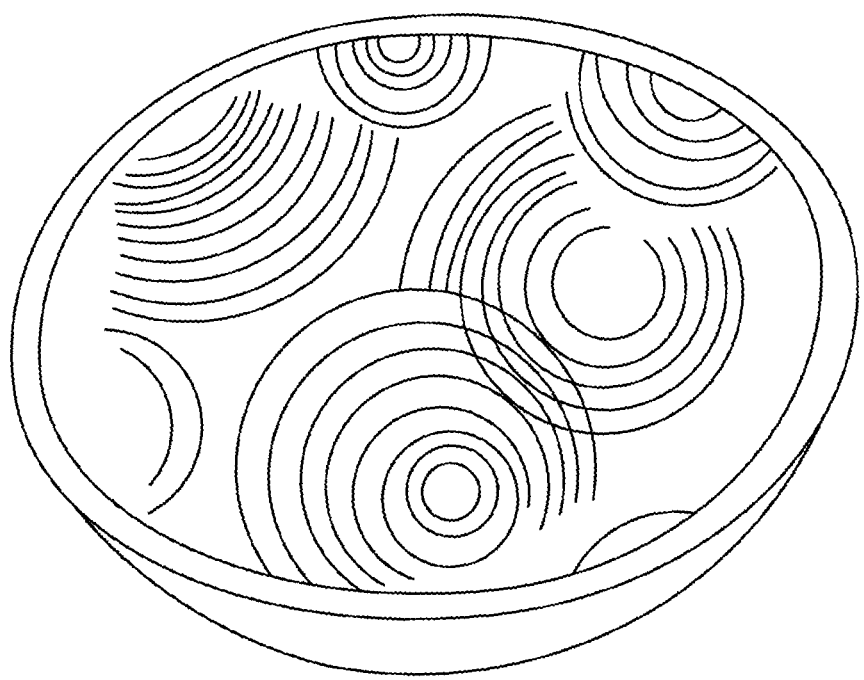
FIG. 1 illustrates an exemplary cross sectional view of internal structure of a three dimensional (3D) prosthesis according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various embodiments disclosed herein provide a novel internal architecture for prostheses and methods of manufacturing thereof. Referring now to the drawings, and more particularly to FIGS. 1 to 4, where similar reference characters denote corresponding features consistently throughout the figures, preferred embodiments are shown.

FIG. 1 illustrates an exemplary cross sectional view of internal architecture of a three dimensional (3D) prosthesis according to an embodiment herein. The exemplary prosthesis is for replacing a breast tissue. The prosthesis illustrates an contour outline and internal three dimensional architecture illustrating a plurality of voids separated by a plurality of internal walls. The void shape, dimensions, thickness of the internal walls are determined based on a young's modulus of elasticity for the person. The void spaces can be filled with one or more of filler materials. In an embodiment, the final prosthesis is designed to have various internal architectures in which voids or empty spaces of various shapes and sizes are formed. Thickness of the silicone material walls making these voids can also be adjusted. Void shape, size and thickness of the walls are the three parameters that can be adjusted to tune the elastic properties, weight and feel of the prosthesis to mimic that of the person using the prosthesis.

In some embodiments, the weight and modulus of elasticity in a person for breast tissue replacement are determined using the historical parameter that includes at least one of age, health, hormonal levels or pregnancy, wherein physical parameters are collected from the potential user of the prosthesis and an outer contour, elasticity, weight collected using actual anatomical structure. Both of these inputs may be determined by a healthcare professional or a prosthesis consultant.

In some embodiments, size and shape of the plurality of void spaces and thicknesses of the plurality of internal walls are same or equal throughout the volume of the prosthesis.

In some embodiments, size and shape of the plurality of void spaces and thicknesses of the plurality of internal walls are not same or equal throughout the volume of the prosthesis and prostheses.

In some embodiments, the internal architecture is incorporated in an prosthesis or prosthesis only to tailor the weight and Young's modulus and shape and size of the prosthesis remain standard.

In some embodiments, the internal architecture is incorporated in an prosthesis or prostheses where shape, size and contour of the prosthesis or prostheses is customized as per the person's 3D contour data and 3D imaging data.

In some embodiments, the internal architecture includes void spaces that are of regular 3-dimensional (3D) polyhedron shapes like tetrahedron, cube, octahedron, dodecahedron, Icosahedron etc.

In some embodiments, the internal architecture includes void spaces that are of various regular shapes like sphere, hemispheres, cylinders, cuboid etc.

In some embodiments, the internal architecture includes void spaces of various regular 3D prism shapes like triangular, rectangular, pentagonal, hexagonal, octagonal etc.

In some embodiments, the internal architecture includes void spaces of various regular 3D pyramid shapes like triangular, rectangular, pentagonal, hexagonal, octagonal etc.

In some embodiments, the internal architecture includes void spaces with various irregular form of aforementioned shapes.

Figure 2A:
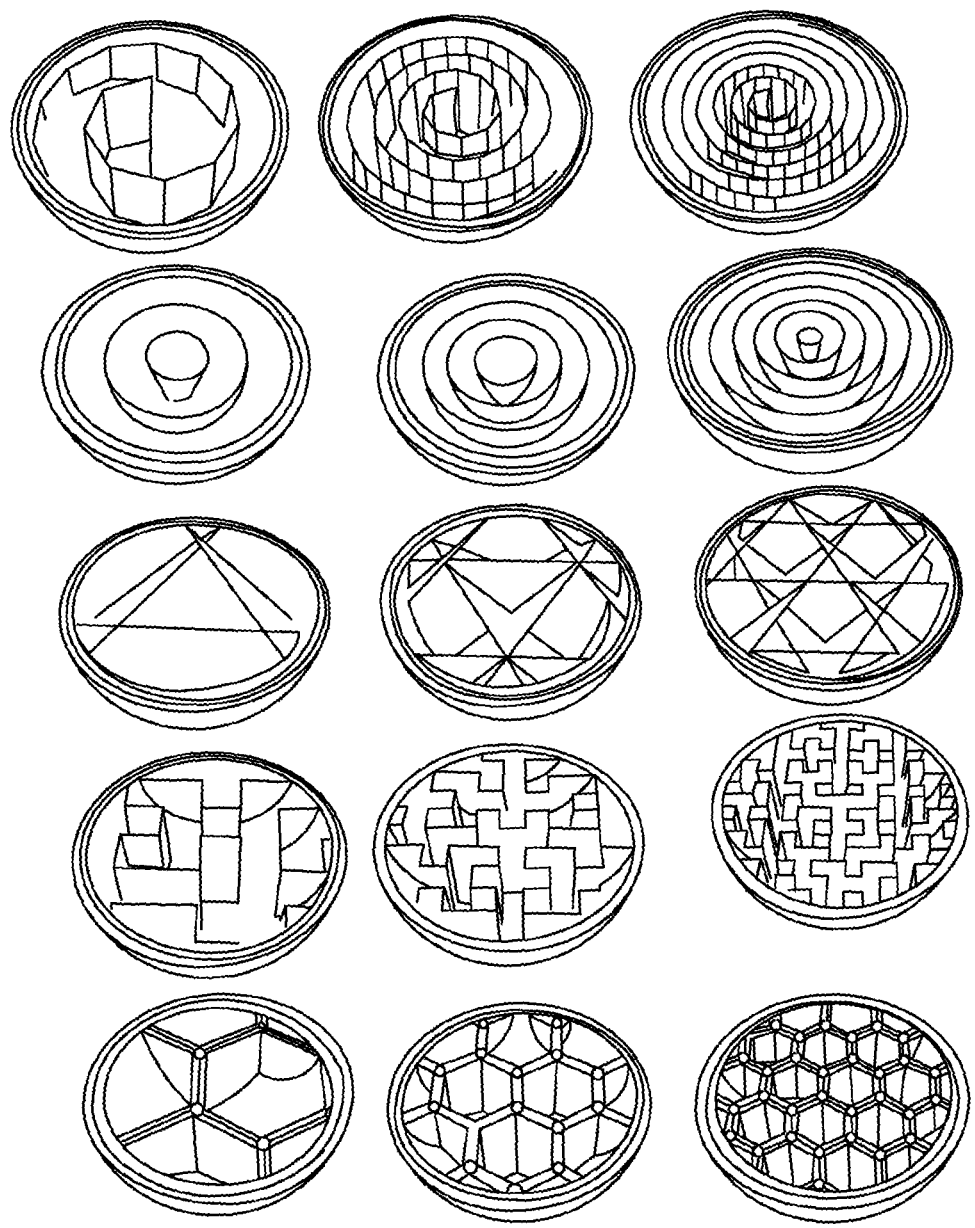
FIGS. 2A and 2B illustrate various exemplary internal structures of a prosthesis according to an embodiment herein.
Figure 2B:
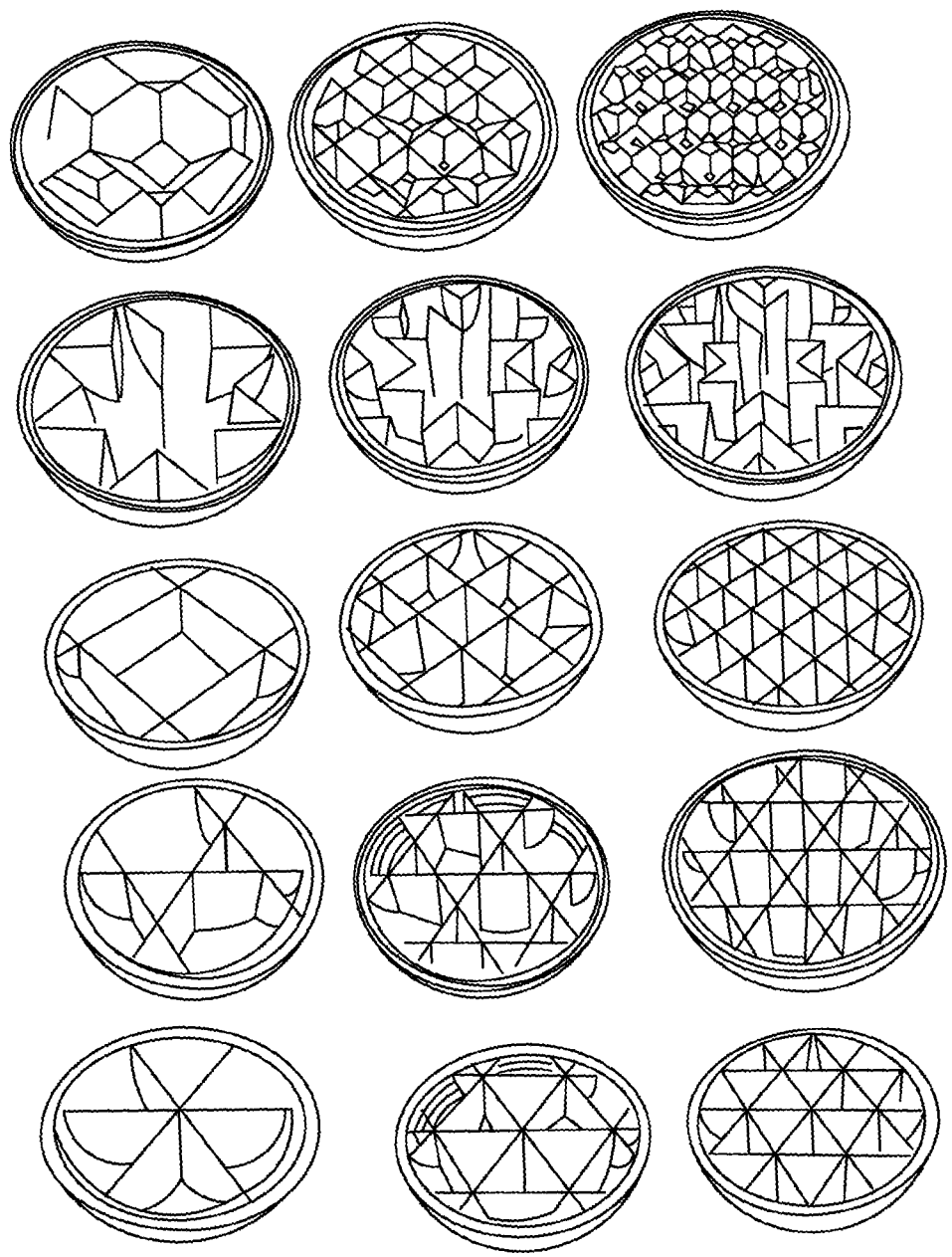

FIGS. 2A and 2B illustrate various exemplary internal architecture of a breast prosthesis according to an embodiment herein. The breast prosthesis is designed to have void spaces of various shapes, sizes, walls making these void space can also be varied. In an aspect, void spaces may not be symmetric structures. In one example, void shape is cubic which is repeated along each sides to fill the prosthesis.

In yet another embodiment, an average perpendicular distance of the adjacent wall of the prosthesis is 2-50 mm. The wall of the prosthesis may not be parallel to each other. Internal architecture makes it possible to tune the elastic properties of the prosthesis to the elastic parameters to the natural tissue. Clinically obtained parameters of the person are considered for the selection of the best internal architecture. The parameters considered in women might be age, health, pregnancy etc. Such parameters are collected from the potential person who may need a prosthesis and an outer contour, elasticity, weight and other physical parameters of the lost or to be lost anatomical structure are measured or predicted from the existing comparable tissues. In case of breast prosthesis, it may be measures taken from the other breast. In an embodiment, a healthcare expert determines the parameters.

Simulation Experiments are performed on the prostheses with different internal architecture and the experimental data is collected pertaining to elasticity, weight and other physical parameters pertaining to a particular type of internal architecture of the prosthesis. Parameters of elasticity and weight are found to be most significant based on the data collected from the persons on the comfort and feel of the prostheses.

In some embodiments, an internal architectures are designed and incorporated into prostheses that replace breast tissue. The isotropic Young's modulus of breast tissue is in the range from 1.5 kPa to 12.0 kPa. Accordingly, the internal architectures of the prostheses are determined to mimic the breast tissue in terms of look and feel which is achieved in an embodiment. Three dimensional internal architecture are determined for the person's Young's modulus and physical parameters in order to achieve same look and feel of the natural anatomical structure. In an embodiment, based on the young's modulus and weight, prostheses are classified into high elastic, low weight; high elastic, medium weight; medium elastic, low weight, medium elastic, medium weight; low elastic, low weight; and low elastic, medium weight. Broadly the internal architectures were classified into high elastic, medium elastic and low elastic. The high elastic prosthesis may include the isotropic Young's modulus in the range from 1 kPa to 2.5 kPa, void dimensions in the range of 35 mm to 50 mm, wall thickness in the range of 0.2 mm to 0.4 mm. The medium elastic prosthesis may include the isotropic Young's modulus in the range from 2.5 kPa to 7.5 kPa, void dimensions in the range of 15 mm to 35 mm, wall thickness in the range of 0.4 mm to 0.8 mm The low elastic prosthesis may include the isotropic Young's modulus in the range from 7.5 kPa to 12.0 kPa, void dimensions in the range of 2 mm to 15 mm, wall thickness in the range of 0.8 mm to 1.0 mm.

| Category | Young's modulus kPa | Weight g | Void Size mm | Wall thickness mm |
| --- | --- | --- | --- | --- |
| High elastic, low weight | 7.5-12.5 | 30-120 | 35-50 | 0.2-0.4 |
| High elastic, medium weight | 7.5-12.5 | 120-300 | 35-50 | 0.2-0.4 |
| High elastic, high weight | 7.5-12.5 | 300-400 | 35-50 | 0.2-0.4 |
| Medium elastic, low weight | 2.5-7.5 | 30-120 | 15-35 | 0.4-0.8 |
| Medium elastic, medium weight | 2.5-7.5 | 120-300 | 15-35 | 0.4-0.8 |
| Medium elastic, high weight | 2.5-7.5 | 300-400 | 15-35 | 0.4-0.8 |
| Low elastic, low weight | 1.5-2.5 | 30-120 | 2-15 | 0.8-1.0 |
| Low elastic, medium weight | 1.5-2.5 | 120-300 | 2-15 | 0.8-1.0 |
| Low elastic, high weight | 1.5-2.5 | 300-400 | 2-15 | 0.8-1.0 |

In an embodiment, based on the internal architecture, the prostheses are classified as given in below table for the corresponding young's modulus and a desired weight of the prosthesis.

| Void Shape | Void Size mm | Weight g | Young's modulus kPa |
|---|---|---|---|
| Conventional Prosthesis | | 262.43 | 15-20 |
| Cubic polygonal | 3.0 | 148.08 | 7.78 |
| | 24.0 | 44.79 | 6.00 |
| | 50.0 | 40.75 | 3.80 |
| Hexagonal | 3.0 | 120.27 | 9.80 |
| | 24.0 | 40.22 | 6.10 |
| | 50.0 | 37.16 | 3.80 |
| Rectangular prism | 3.0 | 67.12 | 10.20 |
| | 24.0 | 36.45 | 7.60 |
| | 50.0 | 35.18 | 4.30 |
| Hexagonal prism | 3.0 | 117.52 | 11.90 |
| | 24.0 | 45.25 | 8.87 |
| | 50.0 | 38.75 | 5.01 |

*All values for a spherical prosthesis of volume 260 cc.

In some embodiments, all or some of the plurality of void spaces are filled with a filler material. All the void spaces in the prosthesis may not contain vacuum at the same time. If so, it will have a tendency to implode inside the body which is dangerous. The filler material may be a gas such as mixture of oxygen ($O_2$) and carbon dioxide ($CO_2$), water vapours and carbon $CO_2$, liquids such as water, saline, silicone gels, fat obtained from person himself or obtained from other natural or synthetic origin, vacuum or any combination of the materials thereof. There are multiple options for fillers based on the desired weight. In some embodiments, fat which can be retrieved from person itself using liposuction, may be used to fill the prosthesis. In another embodiment, saline or saline vapour may be used which may or may not be pressurized. Volume of saline should be such that the vapor pressure (at 37 C) inside the sealed void should be equal to atmospheric pressure. In another aspect, gases like $O_2$ and $CO_2$ can also be filled as they can get absorbed even if leaked inside. In another embodiment, only selected voids instead of all the voids can be filled with any kind of filler in the prosthesis. In another embodiment, more than one kind of filler materials can also be filled in the same prosthesis. In another embodiment, void spaces may contain vacuum as well as filler material in the same prosthesis. In another embodiment, there may or may not be a specific pattern with respect to each other among the voids that are filled or that are not filled.

In some embodiments, the prosthesis can be used to replace any anatomical part of the body that is made of soft tissue either temporarily or permanently. The internal architecture of the prosthesis may be used for making full size, light weight artificial limbs and prostheses for organs or anatomical parts other than breasts.

In an embodiment, the internal architecture is implemented in fabrication of personalized and liquid less breast prostheses, hip prostheses, lip prostheses, dental prostheses, cheek prostheses, chin prostheses, nose prostheses, ear prostheses or any soft tissue/cartilaginous prostheses.

In some embodiments, the prosthesis can be used along with another suitable material for a weight bearing purpose. The suitable material may be a metal.

In some embodiments, the prosthesis can be used to replace breast of the body either temporarily or permanently.

In some embodiments, 3D contour scanning data, 3D imaging data or an image is taken of the anatomical structure which is symmetrical to an anatomical structure that is lost. In one example, mirror inverted data of the data taken is used as an input for process of for manufacturing the prosthesis. Outer contour of the mirror inverted data is lineated.

Figure 3:
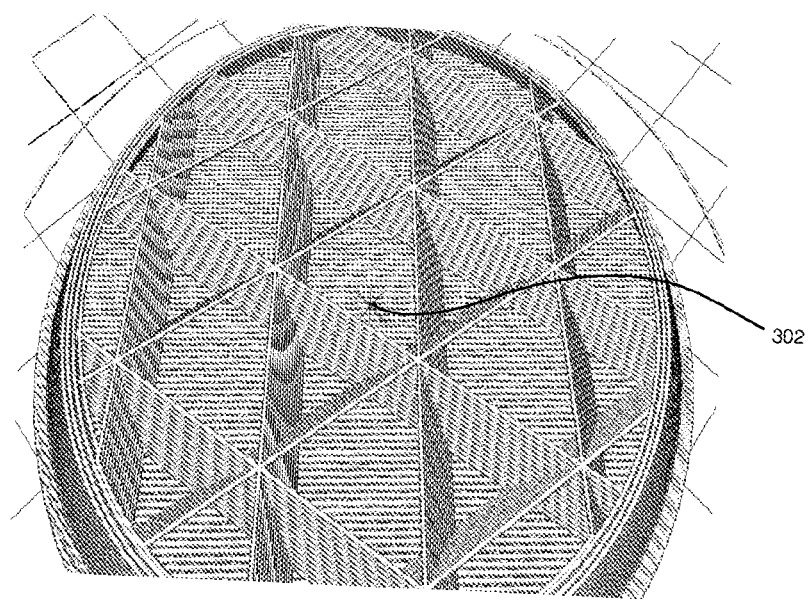
FIG. 3 illustrates an example of prosthesis prepared to receive filler material according to an embodiment herein.

FIG. 3 illustrates an example of prosthesis prepared to receive filler material according to an embodiment herein. 302 illustrates void spaces to be filled with a filler material. In an example, a person requires a breast prosthesis. The physical parameters for the person are determined to be of volume 300 cc, weight 275 g and Young's modulus 7 kPa. Requirement falls in the 'Medium elastic, medium weight' category. For manufacturing the prosthesis, cubic void shape is chosen for this category due to its fit to the category in terms of elasticity to weight ratio. As per the table 2, void size of 30 mm is chosen. As filler material saline is selected as an example. In an embodiment, saline is filled in alternate cubic voids to match the weight of the prosthesis. Wall thickness for each void is 0.6 mm whereas the outer shell is 1.0 mm thick. The aforementioned parameters when combined to manufacture a breast prosthesis give the desired properties which are 300 cc volume, 275 g weight and Young's modulus 7 kPa using a silicone material of Young's modulus 100 kPa.

In some embodiments, the prosthesis is adjusted as per the person's needs and input from the clinicians by tailoring the weight and Young's modulus.

Figure 4:
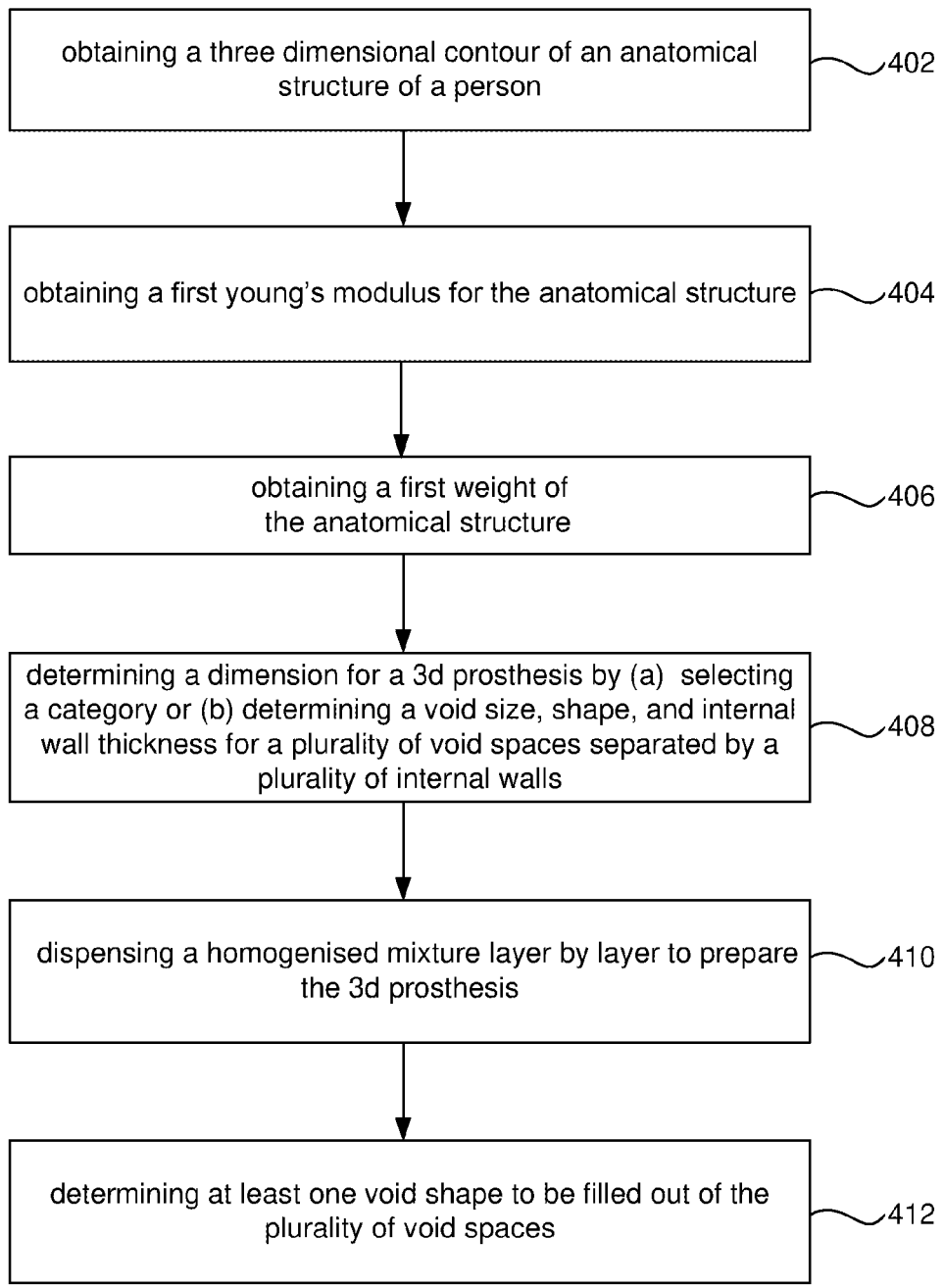
FIG. 4 illustrates a process of manufacturing a breast prosthesis according to an embodiment herein.

FIG. 4 illustrates a process of manufacturing a prosthesis according to an embodiment herein. As an example, when a female suffering from a breast defect or breast cancer visits a clinic for treatment, the female at block 404 may be suggested to undergo a breast removal surgery/mastectomy. As can be appreciated, in the example the female may be an individual entity and the individual entity may be either of a male or a female. In this scenario, a disclosed method for manufacturing a designed 3D prosthesis using a silicone 3D printer may be used. At block 406, a 3D scanning of existing breasts of the female may be performed. The 3D scanning may include determining a 3D contour of an anatomical structure of the female, wherein the 3D contour may be generated using a 3D imaging data. A first Young's modulus of elasticity specific to the anatomical structure of the female may be obtained. Also, a first weight of the anatomical structure of the female may be obtained. Subsequent to performing the 3D scanning, a 3D imaging data of the breasts may be obtained at block 408. The 3D scanning includes determining a dimension of the designed 3D prosthesis wherein an external contour of the designed 3D prosthesis matches the 3D contour of the anatomical structure of the female, and a 3D internal architecture may be incorporated including a plurality of void spaces separated by a plurality of internal walls wherein the 3D internal architecture is selected to match the first Young's modulus of elasticity specific to the anatomical structure of the female by (a) selecting a void size; a void shape; and an internal wall thickness for the plurality of void spaces or (b) determining a category of 3D internal architecture based on at least one of (i) the first weight of an anatomical structure and (ii) the first Young's modulus of elasticity for the anatomical structure.

At block 410, a mirror 3D imaging data is obtained, and a silicone 3D printing of breast prosthesis with respect to the mirror 3D imaging data is obtained at block 412. The silicone 3D printing may be done using a silicone 3D printer. The 3D printer dispenses a homogenized biocompatible mixture layer by layer to print the designed 3D prosthesis, wherein the homogenized biocompatible mixture may be deposited according to the determined dimension of the designed 3D prosthesis, and at least one of a void space is determined and filled with a filler material from the plurality of void spaces.

The 3D printed breast prosthesis thus obtained may be used at block 414 during breast reconstruction surgery. Also, breast prosthesis may be obtained directly by 3D scanning of the existing breast at the block 406, and the same may be used for breast reconstruction surgery at the block 414. Further, 3D scanning of the breasts may be performed at block 416, and a 3D imaging data of the breasts may be obtained at block 418. At block 422, a silicone 3D printing of the 3D imaged data of the breasts is performed. The silicone 3D printed breast prosthesis may be used during a personalized breast implant at block 424, and the personalized 3D printed breast prosthesis may be used during breast reconstruction surgery at block 426. Additionally, the 3D scanning of the breasts at block 416 may be followed by a breast removal surgery/mastectomy at block 420. After performing the breast removal surgery/mastectomy, a breast reconstruction surgery may be performed at block 426. The breast reconstruction surgery performed at steps 426 and 428 may lead to restoring a breast appearance for the female.

In some embodiments, the prosthesis is manufactured using any form of additive manufacturing.

In some embodiments, the prosthesis is manufactured using fused deposition modelling technique of additive manufacturing.

In some embodiments, the prosthesis is manufactured using any biocompatible material that is suitable such as prosthesis grade silicone or polyurethane or any other polymer or combination of polymers of natural or synthetic origin, hydrogel or a combination of hydrogels of natural or synthetic origin or any combinations of materials thereof.

In some embodiments, for external prostheses any suitable material such as silicone or polyurethane or any rubber material or any polymer or combination of polymers of natural or synthetic origin, hydrogel or a combination of hydrogels of natural or synthetic origin or any combinations of materials thereof is used.

In an embodiment, the manufacturing method is implemented in fabrication of pre-surgical models for training and rehearsal purpose.

In an embodiment, the manufacturing method is implemented in fabrication of personalized, lightweight, wearable breast shapers with desired feel and elasticity.

The prostheses are made with minimal time using additive manufacturing wherein the prosthesis material is deposited layer by layer to prepare three dimensional prosthesis with internal architecture to match Young's modulus of the anatomical structure to be replaced. Further it also matches the shape of the outer contour, weight and other physical parameters using an approved and a safe prosthesis material for a human body. It reduces waiting time and psychological trauma associated with a lost body part. The unique internal architecture of the prosthesis is tailored to achieve the desired elastic and mechanical properties close to natural anatomical structure of the person. There is better acceptance psychologically and physiologically which helps in better prophylactic outcome. At the same time by it eliminates the risk of leakage when the prosthesis is implanted into the person's body. Further, the internal architecture of the prosthesis reduces an overall weight of the prosthesis and addresses issues post reconstruction surgeries. It eliminates discomfort and has much better acceptance physiologically and psychologically as it mimics the natural anatomical structure in look and feel. Also, this approach eliminates risk of post-operative tumour growths.

The foregoing description of the specific embodiments will so fully reveal the general nature of the embodiments herein that others can, by applying current knowledge, readily modify and/or adapt for various applications without departing from the generic concept, and, therefore, such adaptations and modifications should be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

I claim:

1. A method for manufacturing a designed three dimensional prosthesis using a silicone 3D printer, wherein the method comprises the steps of:
    obtaining a three-dimensional contour of an anatomical structure of a person, wherein the three-dimensional contour is generated using a 3D imaging data;
    obtaining a first Young's modulus of elasticity specific to the anatomical structure of the person;
    obtaining a first weight of the anatomical structure of the person;
    characterized in that,
    determining a dimension of the designed three dimensional prosthesis, wherein an external contour of the designed three dimensional prosthesis matches the generated three-dimensional contour of the anatomical structure of the person and a three dimensional internal architecture is incorporated comprising of a plurality of void spaces separated by a plurality of internal walls wherein the three dimensional internal architecture is selected to match the first Young's modulus of elasticity specific to the anatomical structure of the person by
        (a) selecting a void size; a void shape; and an internal wall thickness for the plurality of void spaces or
        (b) determining a category of three dimensional internal architecture based on at least one of (i) the first weight of an anatomical structure and (ii) the first Young's modulus of elasticity for the anatomical structure;
    dispensing a homogenized biocompatible mixture layer by layer using the 3D printer to print the designed three dimensional prosthesis, wherein the homogenized biocompatible mixture is deposited according to the determined dimension of the designed three dimensional prosthesis; and
    determining at least one void space to be filled with a filler material from the plurality of void spaces.

2. The method as claimed in claim 1, wherein the homogenized mixture is silicone and cross linker in a ratio of 1:1 to 100:1.

3. The method as claimed in claim 1, wherein the method further includes (a) capturing the three-dimensional contour and 3D imaging data of anatomy of a body part to be replaced, or (b) capturing the three-dimensional contour and 3D imaging data of anatomy of an existing symmetrical body part.

4. The method as claimed in claim 1, wherein the first weight of the anatomical structure of the person is matched to a second weight of the printed three-dimensional prosthesis.

5. The method as claimed in claim 1, wherein the anatomical structure of the person to be replaced is a breast tissue wherein an isotropic Young's modulus of the breast tissue ranges from 1.5 Kilo Pascal (kPa) to 12.0 kPa.

6. The method as claimed in claim 1, wherein dispensing the homogenized mixture further comprises the steps of:

(a) dispensing a silicone elastomer through a first extruder of the silicone 3D printer using a first miniaturized progressive cavity pump;
(b) dispensing a cross-linker through a second extruder of the silicone 3D printer using a second miniaturized progressive cavity pump into a static homogenizer mixer for homogenization; and
(c) depositing the dispensed silicon elastomer and the dispensed cross-linker to print the designed three dimensional prosthesis by depositing one layer on another layer starting from a broader dimension of the designed three-dimensional prosthesis.

7. The method as claimed in claim 1, wherein the internal walls of the prosthesis have an average perpendicular distance in a range of 2 mm to 50 mm.

8. The method as claimed in claim 1, wherein the internal wall thickness is in a range of 0.2 mm to 1.0 mm.

9. The method as claimed in claim 1, wherein the category of three dimensional internal architecture is determined based on the Young's modulus and weight as (a) high elastic, low weight; (b) high elastic, medium weight; (c) high elastic, high weight; (d) medium elastic, low weight; (e) medium elastic, medium weight; (f) medium elastic, high weight; (g) low elastic, low weight; (h) low elastic, medium weight; and (i) low elastic, high weight.

10. The method as claimed in claim 1, wherein the silicone 3D printer prints the designed three dimensional silicone prosthesis for breasts.

* * * * *